(12) United States Patent
Wang et al.

(10) Patent No.: US 9,427,432 B2
(45) Date of Patent: Aug. 30, 2016

(54) BERBERINE FORMULATIONS AND USES THEREOF

(71) Applicant: TWi Biotechnology, Inc., Taipei (TW)

(72) Inventors: Pao-Li Wang, Taipei (TW); Way-Yu Lin, Arlington, TX (US); Chen-Mao Lin, Taipei (TW); Po-Yuan Tseng, Taipei (TW)

(73) Assignee: TWi Biotechnology, Inc., Taipei (TW)

( * ) Notice: Subject to any disclaimer, the term of this patent is extended or adjusted under 35 U.S.C. 154(b) by 0 days.

(21) Appl. No.: 14/576,476

(22) Filed: Dec. 19, 2014

(65) Prior Publication Data

US 2015/0174109 A1  Jun. 25, 2015

Related U.S. Application Data

(60) Provisional application No. 61/918,033, filed on Dec. 19, 2013.

(51) Int. Cl.

| | |
|---|---|
| *A01N 43/42* | (2006.01) |
| *A61K 31/44* | (2006.01) |
| *A61K 31/4375* | (2006.01) |
| *A61K 47/20* | (2006.01) |
| *A61K 47/10* | (2006.01) |
| *A61K 9/00* | (2006.01) |
| *A61K 47/12* | (2006.01) |
| *A61K 47/44* | (2006.01) |

(52) U.S. Cl.
CPC .......... *A61K 31/4375* (2013.01); *A61K 9/0014* (2013.01); *A61K 47/10* (2013.01); *A61K 47/12* (2013.01); *A61K 47/20* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,760,096 A * | 6/1998 | Thornfeldt et al. | 514/772 |
| 6,008,356 A | 12/1999 | Kim et al. | |
| 6,440,465 B1 | 8/2002 | Meisner | |
| 6,974,799 B2 | 12/2005 | Lintner | |
| 2003/0031727 A1 * | 2/2003 | Hahn et al. | 424/617 |
| 2004/0146539 A1 | 7/2004 | Gupta | |
| 2005/0158404 A1 | 7/2005 | Goodless | |
| 2006/0269485 A1 | 11/2006 | Friedman et al. | |
| 2012/0165357 A1 | 6/2012 | Hung et al. | |

FOREIGN PATENT DOCUMENTS

| | | |
|---|---|---|
| EP | 1080719 | 3/2001 |
| WO | WO 2011000218 A1 * | 1/2011 |

OTHER PUBLICATIONS

ISR and Written Opinion in corresponding Application No. PCT/US2014/071364 issued Mar. 18, 2015.
Wollenberg, A et al.; "Cutaneous side effects of EGFR inhibitors—appearance and management"; Dtsch Med Wochenschr., Jan. 2010; 135(4):149-54.
Curry, J et al.; "Dermatologic toxicities to targeted cancer therapy: shared clinical and histologic adverse skin reactions"; Int. Journal of Derm., 2014; 53:376-384.
Lacouture, M et al.; "A proposed EGFR inhibitor dermatologic adverse event-specific grading scale from the MASCC skin toxicity study group"; Support Care Cancer, 2010; 18:509-0522.

* cited by examiner

*Primary Examiner* — Jared D Barsky
(74) *Attorney, Agent, or Firm* — Wood, Phillips, Katz, Clark & Mortimer

(57) ABSTRACT

Pharmaceutical compositions comprising berberine for treatment of skin disorders and methods of use thereof.

6 Claims, 2 Drawing Sheets
(2 of 2 Drawing Sheet(s) Filed in Color)

BERBERINE FORMULATIONS AND USES THEREOF

BACKGROUND OF THE INVENTION

Red face related skin disorders, which share symptomatic similarities and probably pathological causes, include rosacea, acne vulgaris, seborrheic dermatitis, photodermatitis and contact dermatitis. These red face related conditions may range from feelings of heat and sensitivity to flushing or burning with intense sensitivity. Patients with red face related skin disorders often exhibit extreme sensitivity to environmental and topical factors. Steroid-induced rosacea-like dermatitis (or steroid rosacea) is a papular or pustular lesions with erythematous and edematous base with or without telangiectasia, which is caused by prolonged application of topical steroids to the face or as a rebound condition after discontinuation of topical steroids.

Dermatologic toxicities are known cutaneous adverse events associated with targeted therapies or immunotherapy and share similar symptoms and probable pathologic causes of the red face-related skin disorders. Targeted therapies such as epidermal growth factor receptor (EGFR), multityrosine kinase (MTK), MEK, phosphoinositide 3-kinase (PI3K), protein kinase B (AKT), and BRAF inhibitors could induce toxicities including papulopustular rash, maculopapular rash, erythema, telangiectasias flushing, paronychia and fissure, hair changes, xerosis, mucositis, pruritus, and hand-foot skin reaction, which may occur in more than 90% of patients and may also superinfected with bacteria, such as *staphylococcus aureus*. (Wollenberg A, Kroth J et al, 2010; Lacouture M E, Maitland M L et al, 2010; Curry J. L., Torres-Cabala C. A., et al., 2014). Histopathologic findings of such skin toxicities showed that inflammation is frequently involved and leads to acneiform skin rash. A papulopustular rash was more frequently reported on EGFR inhibitors like cetuximab (83% of patients) and afatinib (90% of patients), and MEK inhibitors like selumetinib (93% of patients) and trametinib (80% of patients) therapy. A maculopapular rash was more commonly described with PI3K inhibitors like BKM-120 (37% of patients) and MK2206 (52% of patients) therapy.

Berberine (Natural Yellow 18, 6-dihydro-9,10-dimethoxybenzo(g)-1,3-benzodioxolo (5,6-a) quinolizinium) is an isoquinoline alkaloid present in herb plants, such as coptis (Coptidis rhizome), phellodenron, *Scutellaria baicalensis, Mahonia aquifolium* and *berberis*. Berberine and its derivatives have been found to have antimicrobial and antimalarial activities. It can act against various kinds of pathogens such as fungi, saccharomycete, parasite, bacterium and virus.

Berberine also has anti-inflammatory function, yet the exact mechanism is unknown.

U.S. Pat. No. 6,440,465 pertains to topical skin formulations of glucosamine in an emollient base which contains berberine for the treatment of psoriasis. U.S. Patent Application Publication No. 20050158404 pertains to a nutritional product, dietary supplement or pharmaceutical composition which contains vitamin A, vitamin E, selenium, vitamin B6, zinc, chromium, and a herbal source of berberine for the treatment of acne in oral administration. U.S. Pat. No. 6,974,799 relates to topical compositions comprising a tripeptide (N-palmitoyl-Gly-His-Lys) and a tetrapeptide (N-palmitoyl-Gly-Gln-Pro-Arg) for the treatment of visible signs of aging including wrinkles, stretch marks, dark circles. The formulation may contain additional ingredients, including berberine. In these inventions, berberine is included as one of the many ingredients and its concentration is not specified.

US Patent Application Publication No. 2004/0146539 relates to topical nutraceutical compositions with body slimming and tone-firming anti-aging benefits that may be used to treat skin aging, skin wrinkle, skin exfoliating, acne, rosacea and other skin problems. The composition of this invention includes antimicrobial agents selected from several agents including berberine. In these nutraceutical compositions, berberine is included as one of the many ingredients and its concentration is not specified. There has been a 10% *Mahonia aquifolium* cream (Relieva™, Apollo Pharmaceutical Canada Inc) containing 0.1% berberine for the treatment of psoriasis.

US Patent Application Publication No. 2012/0165357 discloses the use of berberine to treat various red face related skin disorders but it does not disclose any specific formulations of berberine that would be found to be effective for the treatment of specific conditions. Further, it is known that berberine cannot easily efficiently penetrate the skin, and therefore it is likely to be instantly released into the tissue resulting in a temporary effect.

Therefore, there is still a need to develop new effective formulations of berberine for the treatment of various red face related skin disorders.

SUMMARY OF THE INVENTION

The present invention provides pharmaceutical compositions for the treatment and/or prevention of red face related skin disorders. The provided formulations are either cream-based (i.e., cream) formulations or gel-based formulations.

In particular, the invention provides a pharmaceutical composition comprising berberine, wherein said composition is a cream formulation comprising a water phase and an oil phase.

In one embodiment, the concentration of berberine in the provided cream formulations is between 0.01% and 10%, preferably between 0.01% and 1% w/w, preferably 0.01% and 0.3% w/w, more preferably between 0.1% and 0.2% w/w, even more preferably between 0.1% and 0.15% w/w, and most preferably about 0.12% w/w.

All w/w amounts in this application refer to weight by total weight of the formulation.

The pharmaceutical compositions of the invention may further comprise a penetration enhancer.

In one embodiment, the penetration enhancer is an anionic penetration enhancer.

In another embodiment, the penetration enhancer comprises Tween® 60 and glycerin.

In one embodiment, berberine is the only pharmaceutically active component in the provided formulations.

In one embodiment, the pharmaceutical compositions of the invention have a pH of between about 4 and about 7, and more preferably of about 5.5.

In a preferred embodiment, the invention provides a pharmaceutical composition comprising berberine as the only pharmaceutically active component, wherein said berberine is at a concentration of between 0.1% and 0.2% w/w, wherein said composition is a cream formulation comprising a water phase and an oil phase, wherein said composition comprises a penetration enhancer, a preservative, and a stabilizer, and wherein said composition has a pH of between about 4 and about 7.

In an even more preferred embodiment, the invention provides a pharmaceutical composition comprising berberine as the only pharmaceutically active component, wherein said berberine is at a concentration of about 0.12% w/w, wherein said composition is a cream formulation comprising a water phase and an oil phase, wherein said composition comprises a penetration enhancer, a preservative, and a stabilizer, and wherein said composition has a pH of about 5.5.

In another embodiment, the invention provides a pharmaceutical composition comprising berberine, wherein said composition is a gel-based formulation, wherein said composition comprises an anionic penetration enhancer.

In a preferred embodiment, the anionic penetration enhancer comprises sodium dodecyl sulfate (SDS).

In one embodiment, in the gel-based pharmaceutical compositions provided by the invention, about 90% of an average particle size of the berberine is less than 10 µm.

In another embodiment, in the gel-based pharmaceutical compositions provided by the invention, about 50% of an average particle size of the berberine is less than 4 µm.

In one embodiment, the concentration of berberine in the provided gel-based formulations is between 0.01% and 0.3% w/w, more preferably between 0.1% and 0.2% w/w, even more preferably between 0.1% and 0.15% w/w, and most preferably about 0.12% w/w.

The invention also provides methods of treating a red face related skin disorder comprising administering to a patient in need thereof a pharmaceutically effective amount of the pharmaceutical composition of the invention.

In one embodiment, red face related skin disorder is selected from the group consisting of rosacea, acne vulgaris, seborrheic dermatitis, photodermatitis, contact dermatitis, steroid-induced rosacea-like dermatitis, and epidermal growth factor receptor (EGFR) inhibitors-induced skin disorder.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
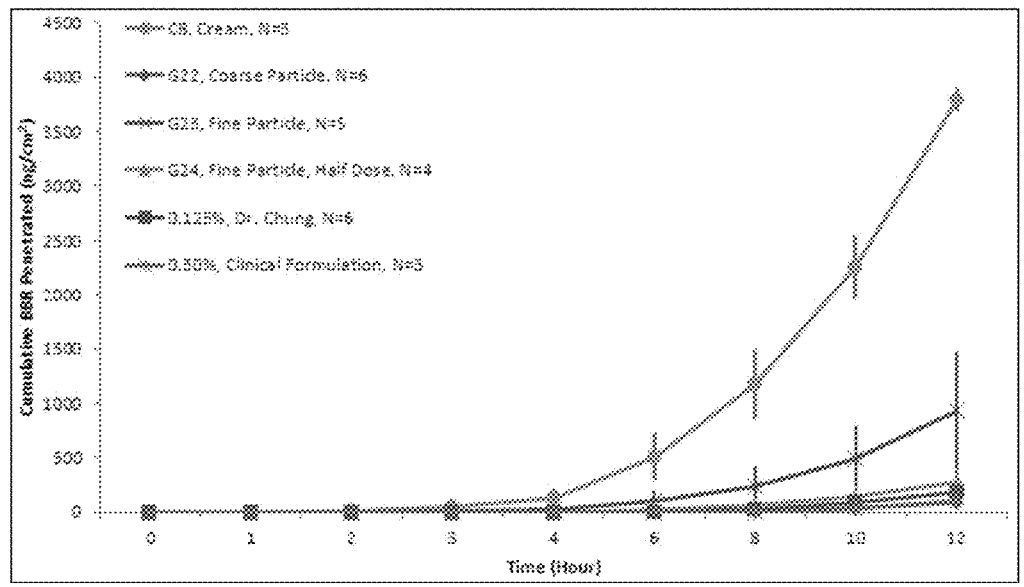
FIG. 1 is a plot of cumulative berberine penetrated (ng/cm$^2$) vs time for six tested formulations of berberine.

Depending on a particular disorder being treated, it is important that berberine can efficiently penetrate the skin. Berberine is a hydrophilic compound (diffusion coefficient of 1.07) which makes it hard for berberine to penetrate through the stratum corneum (SC) to reach the target site, e.g. dermis or epidermis, where red face related skin disorders or targeted therapy-induced dermatologic toxicities may occur. Further, berberine is rather soluble (solubility of 1.57 mg/ml) and will therefore be quickly released into the target cells, leading to a temporary effect.

The present invention thus provides pharmaceutical compositions having an improved penetration rate of berberine for the treatment and/or prevention of red face related skin disorders. The provided formulations are either cream-based (i.e., cream) formulations or gel-based formulations.

In particular, the invention provides a pharmaceutical composition comprising berberine, wherein said composition is a cream formulation comprising a water phase and an oil phase.

Because the cream formulations of the invention may promote the penetration of berberine into the skin, a relatively small amount of berberine is sufficient to achieve desired treating effects. In one embodiment, the concentration of berberine in the provided cream formulations is between 0.01% and 10% w/w, preferably between 0.01% and 1% w/w, preferably 0.01% and 0.3% w/w, more preferably between 0.1% and 0.2% w/w, even more preferably between 0.1% and 0.15% w/w, and most preferably about 0.12% w/w, on the basis of the total weight of the formulation.

The pharmaceutical compositions of the invention may further comprise a penetration enhancer.

In one embodiment, the penetration enhancer is an anionic penetration enhancer. For example, the anionic penetration enhancer may comprise sodium dodecyl sulfate (SDS).

In another embodiment, the penetration enhancer comprises Tween® 60 and glycerin. The cream formulations of the invention preferably include Tween® 60 and glycerin as penetration enhancers. When the same penetration enhancers are used in non-cream formulations, they do not result in an improved penetration rate, suggesting that there is something unique about the cream-based formulations.

In one embodiment, berberine is the only pharmaceutically active component in the provided formulations.

In one embodiment, the pharmaceutical compositions of the invention have a pH of between about 4 and about 7, and more preferably of about 5.5.

In a preferred embodiment, the invention provides a pharmaceutical composition comprising berberine as the only pharmaceutically active component, wherein said berberine is at a concentration of between 0.1% and 0.2% w/w, wherein said composition is a cream formulation comprising a water phase and an oil phase, wherein said composition comprises a penetration enhancer, a preservative, and a stabilizer, and wherein said composition has a pH of between about 4 and about 7.

In an even more preferred embodiment, the invention provides a pharmaceutical composition comprising berberine as the only pharmaceutically active component, wherein said berberine is at a concentration of about 0.12% w/w, wherein said composition is a cream formulation comprising a water phase and an oil phase, wherein said composition comprises a penetration enhancer, a preservative, and a stabilizer, and wherein said composition has a pH of about 5.5.

It was very surprisingly and unexpectedly found that the cream formulations of the invention have a superior penetration rate compared to non-cream berberine formulations.

In another embodiment, the invention provides a pharmaceutical composition comprising berberine, wherein said composition is a gel-based formulation, wherein said composition comprises an anionic penetration enhancer.

In a preferred embodiment, the anionic penetration enhancer comprises sodium dodecyl sulfate (SDS). Including SDS as an anionic penetration enhancer results in the provided gel-based formulations being hydrophobic (a partition coefficient of 50.1) and having a dramatically lower solubility of about 0.011 mg/ml, allowing for a slow release of berberine into the target cells, resulting in an extended release profile.

It was found in the present invention that, in a pH of between 4 and 7, berberine solubility in the presence of SDS ranges from 0.01 to 0.06 mg/mL, i.e., 25 to 150 times lower than aqueous berberine solubility (1.57 mg/mL), and is relatively low at pH 5.5.

It was surprisingly found that out of all tested penetration enhancers (SDS, glycerol, propylene glycol, PEG 400, ethanol, and Tween®), the addition of SDS in the gel-based formulations resulted in the most enhanced penetration rate and increased local concentration of berberine in epidermis and dermis.

In one embodiment, in the gel-based pharmaceutical compositions provided by the invention, about 90% of an average particle size of the berberine is less than 10 µm.

In another embodiment, in the gel-based pharmaceutical compositions provided by the invention, about 50% of an average particle size of the berberine is less than 4 µm.

It was also surprisingly found that in the gel-based formulations there was a positive correlation between the amount of SDS and the penetration rate, and negative correlation between the size of berberine and the penetration rate.

Because the gel-based formulations of the invention may promote the penetration of berberine into the skin, a relatively small amount of berberine is sufficient to achieve desired treating effects. In one embodiment, the concentration of berberine in the provided gel-based formulations is between 0.01% and 0.3% w/w, more preferably between 0.1% and 0.2% w/w, even more preferably between 0.1% and 0.15% w/w, and most preferably about 0.12% w/w, on the basis of the total weight of the formulation.

The invention also provides methods of treating a red face related skin disorder comprising administering to a patient in need thereof a pharmaceutically effective amount of the pharmaceutical composition of the invention.

In one embodiment, red face related skin disorder is selected from the group consisting of rosacea, acne vulgaris, seborrheic dermatitis, photodermatitis, contact dermatitis, steroid-induced rosacea-like dermatitis, and epidermal growth factor receptor (EGFR) inhibitors-induced skin disorder.

The invention further provides methods of treating and/or preventing targeted therapy-induced dermatologic toxicities comprising administering to a patient in need thereof a pharmaceutically effective amount of the pharmaceutical composition of the invention.

In one embodiment, said targeted therapy is selected from the group consisting of EGFR, multityrosine kinase (MTK), MEK, phosphoinositide 3-kinase (PI3K), protein kinase B (AKT), and BRAF inhibitors; and said targeted therapy-induced dermatologic toxicity is selected from the group consisting of papulopustular rash, maculopapular rash, erythema, telangiectasias flushing, paronychia and fissure, hair changes, xerosis, mucositis, pruritus, and hand-foot skin reaction.

The concentrations of berberine in epidermis, dermis, and receiver (which refers to a container filled with PBS that in contact with the skin) are measured by the following approach. Franz diffusion cell setup is essentially a piece of skin clamped between two clamps. The drug is applied on one side of the skin (top) and drug concentration is measured in the received portion (bottom) of the setup.

As used herein, the term "penetration rate" refers to an amount of berberine that presents in per gram of epidermis or dermis tissue, or an amount of berberine per $cm^2$ of skin that presents in the receiver, after a certain time period from the application of a formulation to the skin.

Amount of the drug measured in the receiver indicates the total amount that penetrated through SC, epidermis and dermis region of the skin. The pharmaceutical composition of the present invention has improved penetration rate, and the preferred range of the penetration rate is as follows:

Epidermis: 0.4 to 4000 µg of berberine per gram of tissue
Dermis: 0.003 to 30 µg of berberine per gram of tissue
Receiver: 0.0001 to 1 µg of berberine per 1×1 $cm^2$ of skin.

The following Table 1 lists various ingredients that may be used in the compositions of the invention. This list, however, is only provided for illustration purpose, but not to limit the scope of the present invention. Further, different ingredients/excipients can act in more than one way, e.g. can function as a penetration enhancer, an emulsifying agent, a wetting agent, etc.

TABLE 1

| Excipient | Function | Concentration range (%) | Replacements/Analogs |
| --- | --- | --- | --- |
| Sodium Lauryl Sulfate | Anionic penetration enhancer | 0.5-2.5 | Sulfate, Sulfonate, Phosphate, Oleate, monostearate and Carboxylates |
| Carbopol 934P | Gelling agent | 0.3-3 | Carbopol 940, Carbopol 941, Carbopol 971, Carbopol 974, Carbopol 980, |
| Hydroxyethyl Cellulose | Gelling agent | 0.5-8 | Carbopol 981, Carbopol 5984EP, Carbopol ETD 2020, Carbopol 5984EP, Hydroxyethyl cellulose, Hydroxyethylmethyl cellulose, Hydroxypropyl cellulose, Hydroxypropyl cellulose (Low-substituted), Methyl cellulose, Methylhydroxypropyl cellulose |
| Methylparaben Propylparaben | Preservatives | 0.02-0.3 0.01-0.8 | Quaternary ammonium compounds, Amino aryl acid esters, Alkyl/Aryl alcohols, Alkyl/Aryl acids, Alkyl/Aryl amides, Organomercurials, Formaldehyde donators, Biguanides, Phenols |
| EDTA | Antioxidant | 0.005-0.1 | Dipotassium edetate, Disodium edetate, Edetate calcium disodium, Sodium |

TABLE 1-continued

| Excipient | Function | Concentration range (%) | Replacements/Analogs |
|---|---|---|---|
| | | | edetate, Trisodium edetate |
| Glycerin | Humectant | 0.01-30 | Propylene glycol, Polyethylene glycol |
| Tween ® 80 | Wetting agent | 0.1-3 | Polyethylene glycol, Sorbitan esters |
| Citric acid monohydrate | Buffering agent | 0.1-2 | Anhydrous citric acid, Fumaric acid, Malic acid, Sodium citrate dehydrate, Tartaric acid |
| Sodium citrate dihydrate | | 0.3-2 | Anhydrous sodium citrate; citric acid monohydrate |
| Water | Water | — | — |
| Stearic acid | Oil base | 1-20 | Calcium stearate, Magnesium stearate, Polyoxyethylene stearates, Purified stearic acid, Zinc stearate, Lauric acid, Myristic acid, Palmitic acid, Oleic acid |
| Castor oil | Oil base | 5-12.5 | Mineral oil, Castor oil, Almond oil, Cocao oil, Corn oil, Coconut oil, Cotton seed oil, Linseed oil, Olive oil, Soybean oil |
| White petrolatum | Oil base | 4-56 | Yellow petrolatum, Liquid petrolatum, Paraffin, Ceresin, Microcrystalline wax, Plastibase |
| SPAN 60 | Emulsifying agent | 1-15 | Polyoxyethylene sorbitan fatty acid esters, |
| Tween ® 60 | Emulsifying agent | 1-15 | Polyethylene glycol, Sorbitan esters |

As used herein, the term "berberine" refers to 5,6-dihydro-9,10-dimethoxybenzo(g)-1,3-benzodioxolo (5,6-a) quinolizinium. The invention also contemplates the use of analogues of berberine which include but are not limited to jatrorrhizine, palmatine, coptisine, 9-demethylberberine, 9-demethylpalmatine, 13-hydroyberberine, berberrubine, palmatrubine, 9-O-ethylberberrubine, 9-O-ethyl-13-ethylberberrubine, 13-methyldihydroberberine N-methyl salt, tetrahydroprotoberberines and N-methyl salts thereof, 9-lauroylberberubine chloride, and pharmaceutically acceptable salts of all these compounds.

As used herein, the term "pharmaceutically acceptable salts" includes salts of acidic or basic groups. Examples of pharmaceutically acceptable salts include those derived from inorganic acids, such as hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids, such as glucuronic or galacturonic acids and the like.

As used herein, the terms "treatment" and "treating" include inhibiting the disease or condition, causing a reduction in severity and/or frequency of symptoms, elimination of symptoms and/or underlying cause, prevention of the occurrence of symptoms and/or their underlying cause, ameliorating and/or improving a patient's condition. Thus, "treating" a patient with said compositions of the invention includes prevention of a particular disorder in a susceptible individual, as well as management of a clinically symptomatic individual to inhibit or cause regression of a disorder or disease, and maintenance of the current state and/or prevention of a progression of a disorder or disease. Treatment can include prophylaxis, therapy or cure.

As used herein, the term "pharmaceutically effective amount" of the compounds and/or pharmaceutical compositions of the invention refers to a sufficient amount of the compound and/or composition to treat, inhibit, ameliorate or prevent hyperuricemia or metabolic disorders associated with hyperuricemia, at a reasonable benefit/risk ratio applicable to any medical treatment. It will be understood, however, that the total daily usage of the compounds and/or compositions of the present invention will be decided by the attending physician within the scope of sound medical judgment. The specific effective dose level for any particular patient will depend upon a variety of factors, including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the composition at levels lower than required to achieve the desired therapeutic effect and to gradually increase the dosage until the desired effect is achieved.

The pharmaceutical composition can further include a pharmaceutically acceptable carrier, and can be in solid or liquid form, including but not limited to, tablets, powders, capsules, pellets, solutions, suspensions, elixirs, emulsions, gels, creams, patch, or suppositories, including rectal and urethral suppositories.

As used herein, the term "pharmaceutically acceptable carrier" refers to a pharmaceutically acceptable material, composition or vehicle, such as a liquid or solid filler, diluent, excipient, solvent or encapsulating material. A pharmaceutically acceptable carrier is compatible with the other ingredients of the composition, with the mode of administration, and not injurious to the patient. A pharmaceutically acceptable carrier may be either aqueous or non-aqueous. Pharmaceutically acceptable carriers include gums, starches, sugars, cellulosic materials, and mixtures thereof. Some examples of materials which can serve as pharmaceutically-acceptable carriers include, but are not limited to: (a) sugars, such as lactose, glucose and sucrose; (b) starches, such as corn starch and potato starch; (c) cellulose, and its derivatives, such as sodium carboxymethyl cellulose, ethyl cellulose and cellulose acetate; (d) powdered tragacanth; (e) malt; (f) gelatin; (g) talc; (h) excipients, such as cocoa butter and suppository waxes; (i) oils, such as peanut oil, cottonseed oil, safflower oil, sesame oil, olive oil, corn oil and soybean oil; (j) glycols, such as propylene glycol; (k) polyols, such as glycerin, sorbitol, mannitol and polyethylene glycol; (l) esters, such as ethyl oleate and ethyl laurate; (m) agar; (n) buffering agents, such as magnesium hydroxide, aluminum hydroxide, boric acid and sodium borate, and phosphate buffers; (o) alginic acid; (p) pyrogen-free water; (q) isotonic saline; (r) Ringer's solution; (s) ethyl alcohol; (t) phosphate buffer solutions; and (u) other non-toxic compatible substances suitable for use in pharmaceutical compositions.

The compositions of the invention may be administered using any means known in the art, including but not limited to oral, nasal, parenteral, topical, transdermal, or rectal routes of administration. Preferably, the compositions are adapted for oral or topical administration. For example, the active ingredient of the composition can be formulated with suitable excipients for the preparation of tablets, capsules, pellets, troches, lozenges, solutions, powders or granules, suspensions, hard or soft capsules, patches and any other suitable forms.

The following Examples demonstrate some aspects of the invention. The Examples are not meant to limit the invention in any way.

Example 1

Mouse Skin Penetration Study of Berberine Formulations

The following six berberine formulations were compared: C8, 0.125%, 0.3%, G22, G23 and G24.
Formulations
The formulations were as follows:
C8 (a cream-based formulation):
Water Phase
  berberine (0.12%), Tween® 60 (1%), Glycerin (3%), methylparaben (0.1%), propylparaben (0.02%), NaOH (to adjust pH to 5.5), and EDTA (0.02%).
Oil Phase
  stearic acid (7.5%), castor oil (8%), white petrolatum (6%), and SPAN 60 (2%).
0.125% (gel-based formulation):
  berberine (0.125%), ethanol (2.5%), glycerol (10%), phenoxyethanol (0.3%), carbomer.
0.3% (gel-based formulation):
  berberine (0.3%), propylene glycol (9.25%), PEG 400 (5.03%), methylparaben (0.1%), propylparaben (0.02%), NaOH (0.4%), EDTA (0.02%), Carbomer 934P (1%).
G22 (gel-based formulation):
  berberine (0.1%), SDS (0.086%), glycerol (10%), Tween® 80 (0.5%), methylparaben (0.1%), propylparaben (0.02%), citric acid (0.033%), sodium citrate dihydrate (0.115%), NaOH, EDTA (0.02%), Carbomer 934P (0.3%), HEC 250 HHX (1.2%). Particle Size Distribution: 3.83/11.34/27.24 (in the format D10/D50/D90, where each value refers to the respective percentage of particles below the stated size, i.e. 10% of the particles are less than 3.83, and so on).
G23 (gel-based formulation):
  berberine (0.1%), SDS (0.086%), glycerol (10%), Tween® 80 (0.5%), methylparaben (0.1%), propylparaben (0.02%), citric acid (0.033%), sodium citrate dihydrate (0.115%), NaOH, EDTA (0.02%), Carbomer 934P (0.3%), HEC 250 HHX (1.2%). Particle Size Distribution: 1.45/2.85/9.30.
G24 (gel-based formulation):
  berberine (0.1%), SDS (0.043%), glycerol (10%), Tween® 80 (0.5%), methylparaben (0.1%), propylparaben (0.02%), citric acid (0.033%), sodium citrate dihydrate (0.115%), NaOH, EDTA (0.02%), Carbomer 934P (0.3%), HEC 250 HHX (1.2%). Particle Size Distribution: 1.55/2.86/5.44.

The particle size of G22, G23 and G24 formulations were determined as follows.

Purified water was prepared, then berberine chloride, Tween® 80 and sodium lauryl sulfate (SDS) were added. After well dispersed, the mixture was micronized. After that, the particle size was measured by a diffraction analyzer.
Experimental Conditions Mice were sacrificed by cervical dislocation. The full-thickness flank skin was removed and placed on the diffusion cell in contact with receptor phase, which was 0.01M PBS (pH 7.4 at 37° C.). Buffers were pumped through the receiver compartment at a flow rate of 3-4 mL/h. 300 µl of formulations were added onto the skin surface in the donor compartment. Receiver solutions were collected at hour 0, 1, 2, 3, 4, 6, 8, 10, and 12 for HPLC analysis. Skin flux was calculated from slope of the linear part of the cumulative amount berberine chloride penetrated versus time curve.
Results FIG. 1 demonstrates a plot of cumulative berberine penetrated ($ng/cm^2$) vs time for all 6 tested formulations. As one can see, C8 (cream formulation) and G23 (gel-based formulation) penetrated the best as compared to the other formulations. This was unexpected because theoretically, all six formulations should penetrate with a similar rate due to physical properties of berberine in water phase.

Figure 2:
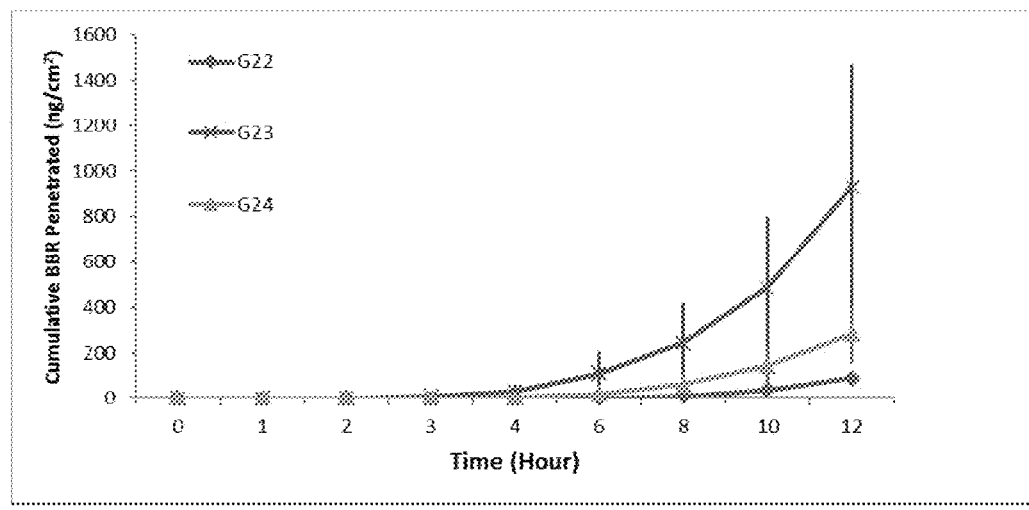
FIG. 2 is a plot of cumulative berberine penetrated (ng/cm$^2$) vs time for three gel suspension formulations of berberine (G22, G23 and G24).

FIG. 2 demonstrates a plot of cumulative berberine penetrated ($ng/cm^2$) vs time for three gel suspension formulations (G22, G23 and G24). As one can see, penetration rate is positively correlated to the penetration enhancer (SDS) but is negatively correlated to berberine size. G23 and G24 with berberine size of D90 less than 10 µm have higher penetration rate than G22 with D90 higher than 10 µm.

Example 2

Mini-Pig Penetration Study of Berberine Formulations

The following berberine formulations were compared: 1) C8, G22, and 023; and 2) 0.125%, 0.30%, and 023.

Skin: Mini-pig (Lanyu pig or Lee sung pig) skin dermatomed to 700 µm with electrical resistance >10 kΩ/ (Millicell-ERS, Millipore).
Penetration Experiments:

Pig skin was placed on the diffusion cell with dermal side in contact with receptor phase, which was filled with PBS (pH 7.4 at 37° C.). 20 µl of formulations were added onto the skin surface in the donor compartment. After 8 hours, the residual formulation on the skin surface was removed using three dry cotton swabs. At the end of 12 and 24 hours of treatment with formulations, skin was dismounted from the diffusion cell, again skin surface was cleaned carefully with three water-soaked cotton swabs. 10 tape-strippings were employed to remove stratum corneum. The skin was then placed on glass disc and heat-separated into epidermis and dermis at 60° C. water bath for 90 seconds. Both the separated epidermis and dermis were weighed and minced, and extracted with 0.5 ml diluent (1% $H_3PO_4$:$CH_3OH$ (1:1)). The skin extracts were centrifuged at 14,500 rpm for 20 min. Berberine chloride concentrations in the receiver solutions and supernatants from skin extracts were determined by HPLC. Recovery of berberine chloride from skin was determined by spiking known amounts of the drug into skin tissues and processed as described above.

Results

Table 2 summarizes the results of this experiment.

TABLE 2

| Run 1 (Comparing C8, G22, G23) | | | |
|---|---|---|---|
| 12 hr | Epidermis (µg/g) | Dermis (µg/g) | Receiver (µg/cm²) |
| C8 | 6.15 | 0.22 | 0.069 |
| G22 | 7.55 | 0.14 | 0.0625 |
| G23 | 11.99 | 0.09 | 0.0025 |
| 24 hr | Epidermis (ug/g) | Dermis (ug/g) | Receiver (ug/cm²) |
| C8 | 14.675 | 0.2 | 0.029 |
| G22 | 30.95 | 0.43 | 0.1905 |
| G23 | 100.315 | 0.64 | 0.0285 |
| Run 2 (Comparing 0.125%, 0.30%, G23) | | | |
| 12 hr | Epidermis (µg/g) | Dermis (µg/g) | Receiver (µg/cm²) |
| 0.125% | 11.67 | 0.14 | 0 |
| 0.30% | 22.09 | 0.41 | 0 |
| G23 | 16.68 | 0.1 | 0 |
| 24 hr | Epidermis (µg/g) | Dermis (µg/g) | Receiver (µg/cm²) |
| 0.125% | 18.74 | 0.19 | 0.01 |
| 0.30% | 39.83 | 0.15 | 0 |
| G23 | 35.75 | 0.27 | 0.009 |

The mini-pig skin penetration results indicate that: a) C8 (cream formulation) penetrates surprisingly well; b) formulations containing berberine particles continuously released over the 24 hours (G22, G23 vs C8, 0.125% and 0.3%); c) G22 & G23 (formulations containing berberine particles) retained more berberine in the epidermis and dermis after 24 hours as compared to C8 (cream formulation); d) formulations containing berberine particles penetrated better than formulations with berberine in solution (G23 vs 0.3%); e) G23 retained approximately the same amount of berberine in the epidermis and more berberine in the dermis after 24 hours as compared to the 0.3% formulation even though G23 contained only 0.1% berberine; and f) compared with other penetration enhancers (ethanol and glycerol in the 0.125% formulation and propylene glycol and PEG 400 in the 0.3% formulation), the addition of SDS in G23 resulted in enhanced penetration rate and increased local concentration of berberine in epidermis and dermis.

Example 3

Skin Biopsy Results from a Patient Treated by Topical Formulation Comprising Berberine The subject tested was a 56 year old male who received afatinib, an EGFRI inhibitor, for treatment of non-small cell lung cancer (NSCLC). Upon receiving afatinib, the subject started applying topical gel of G23 formulation on one side of his face and vehicle gel (G23 with no berberine) on the other side once daily.

Bilateral skin biopsies from nasolabial folds (both sides of the nose) were collected from the subject completing two-week topical treatment. Skin specimens were obtained by incisional biopsy measuring 1.0 cm×0.5 cm, then histologically processed using hematoxylin and eosin (H&E) staining. Evaluation was performed by a trained dermatopathologist.

Figure 3:
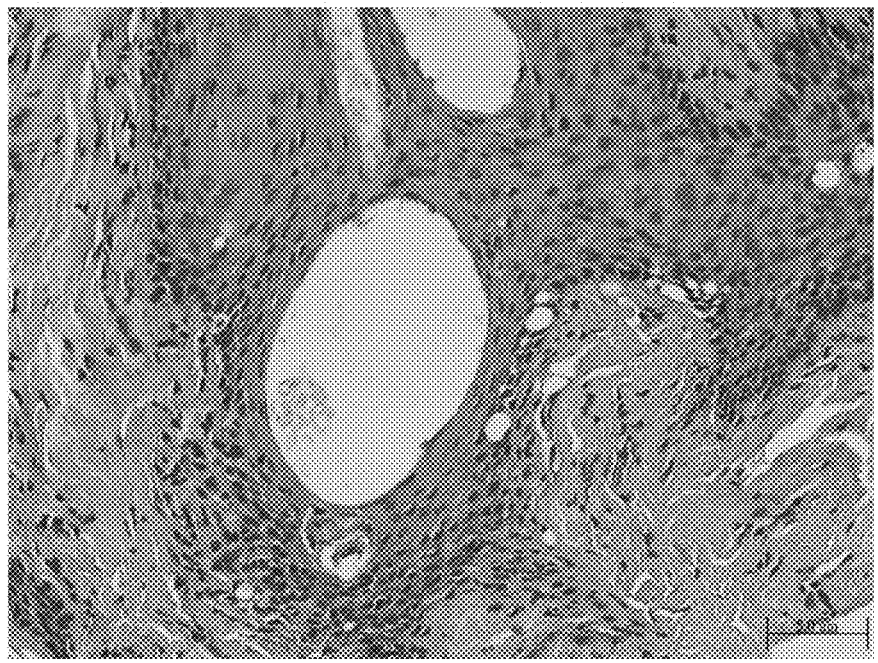
FIG. 3 is a picture showing hematoxylin and eosin (H&E) staining of bilateral skin biopsies from nasolabial folds of a patient receiving afatinib and topically administered with a gel formulation (G23) on one side of his face.
Figure 4:
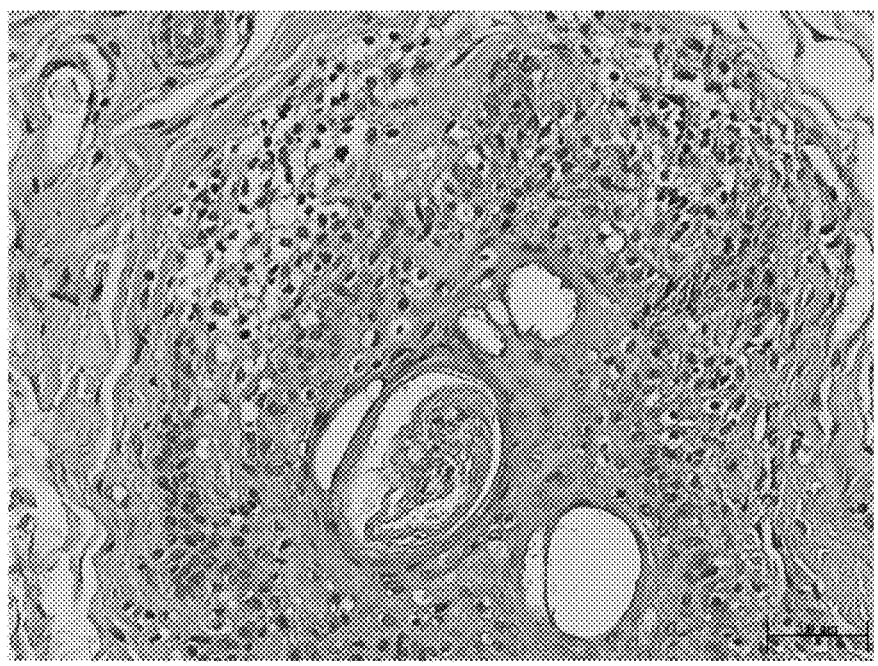
FIG. 4 is a picture showing H&E staining of bilateral skin biopsies from nasolabial folds of the patient receiving afatinib and topically administered with a vehicle gel (G23 without berberine) on the other side of his face.

The H&E staining results (FIGS. 3 & 4) show that follicular structure remains intact and there was no inflammatory cell infiltrate for skin area treated with G23 (FIG. 3) while there was destruction of the follicular structure, profuse infiltration of inflammatory cells at the perifollicular region vacuolar change of the dermal-epidermal junction of follicular epithelium for skin treated with vehicle gel (FIG. 4), indicating potential anti-inflammatory effect of G23 for treating EGFR inhibitor-associated skin toxicity.

What is claimed is:

1. A method of treating and/or preventing dermatologic toxicities induced by a targeted therapy comprising administering to a patient in need thereof a pharmaceutically effective amount of a pharmaceutical composition comprising berberine, wherein said composition is a gel-based formulation, wherein said composition comprises sodium dodecyl sulfate (SDS), wherein about 90% of an average particle size of the berberine is less than 10 µm.

2. A method of treating and/or preventing dermatologic toxicities induced by a targeted therapy comprising administering to a patient in need thereof a pharmaceutically effective amount of a pharmaceutical composition comprising berberine, wherein said composition is a gel-based formulation, wherein said composition comprises sodium dodecyl sulfate (SDS), wherein about 50% of an average particle size of the berberine is less than 4 µm.

3. The method according to claim 1 or 2, wherein the amount of sodium dodecyl sulfate is at a concentration between 0.5% and 2.5% w/w on the basis of the total weight of the formulation.

4. The method according to claim 1 or 2, wherein said targeted therapy is selected from the group consisting of EGFR, multityrosine kinase (MTK), MEK, phosphoinositide 3-kinase (PI3K), protein kinase B (AKT), and BRAF inhibitors, and wherein said targeted therapy-induced dermatologic toxicity is selected from the group consisting of papulopustular rash, maculopapular rash, erythema, telangiectasias flushing, paronychia and fissure, hair changes, xerosis, mucositis, pruritus, and hand-foot skin reaction.

5. The method according to claim 1 or 2, wherein said berberine is at a concentration between 0.01% and 10% w/w on the basis of the total weight of the formulation.

6. The method according to claim 1 or 2, wherein said composition has a pH of between about 4 and about 7.

* * * * *